United States Patent [19]

Szycher

[11] 4,424,335
[45] Jan. 3, 1984

[54] KERATOPROSTHETIC POLYURETHANE

[75] Inventor: Michael Szycher, Lynnfield, Mass.

[73] Assignee: Thermo Electron Corporation, Waltham, Mass.

[21] Appl. No.: 399,881

[22] Filed: Jul. 19, 1982

Related U.S. Application Data

[62] Division of Ser. No. 238,767, Feb. 27, 1981, which is a division of Ser. No. 120,345, Feb. 11, 1980, Pat. No. 4,285,073.

[51] Int. Cl.$^3$ .............................................. C08G 18/32
[52] U.S. Cl. ......................................... 528/77; 528/60; 528/58
[58] Field of Search .................................... 528/60, 77

[56] References Cited

U.S. PATENT DOCUMENTS

| | | | |
|---|---|---|---|
| 2,542,386 | 2/1951 | Beattie | 18/58 |
| 2,714,721 | 8/1955 | Stone | 3/1 |
| 2,754,520 | 7/1956 | Crawford | 3/13 |
| 2,808,391 | 10/1957 | Pattison | 260/77.5 |
| 2,808,967 | 10/1957 | Miller | 222/215 |
| 2,865,940 | 12/1958 | Nobis et al. | 260/453 |
| 2,866,774 | 12/1958 | Price | 260/77.5 |
| 2,899,411 | 8/1959 | Schollenberger | 260/77.5 |
| 2,929,800 | 3/1960 | Hill | 260/77.5 |
| 2,948,691 | 8/1960 | Windenuth et al. | 260/2.5 |
| 2,952,023 | 9/1960 | Rosen | 3/13 |
| 3,012,987 | 12/1961 | Ansul | 260/45.4 |
| 3,130,175 | 4/1964 | Peter et al. | 260/45.4 |
| 3,208,957 | 9/1965 | Powanda et al. | 260/2.5 |
| 3,336,242 | 8/1967 | Hampson et al. | 260/2.5 |
| 3,454,966 | 7/1969 | Rosen | 3/13 |
| 3,458,870 | 8/1969 | Stone | 3/13 |
| 3,487,050 | 12/1969 | Castro et al. | 260/75 |
| 3,512,183 | 5/1970 | Sharp et al. | 3/1 |
| 3,562,352 | 2/1971 | Nyilas | 260/824 |
| 3,604,016 | 9/1971 | Robinson et al. | 3/1 |
| 3,635,904 | 1/1972 | Briggs et al. | 260/77.5 AA |
| 3,746,683 | 7/1973 | Salyer et al. | 260/33.2 R |
| 3,760,045 | 9/1973 | Thiele et al. | 264/1 |
| 3,798,200 | 3/1974 | Kaneko et al. | 260/77.5 AM |
| 3,804,812 | 4/1974 | Koroscil | 260/77.5 AM |
| 3,939,021 | 2/1976 | Nishibayashi et al. | 156/78 |
| 3,961,379 | 6/1976 | Highgate | 3/13 |
| 4,002,169 | 1/1977 | Cupler | 128/276 |
| 4,131,604 | 12/1978 | Szycher | 528/79 |
| 4,131,605 | 12/1978 | Ammons | 528/77 |
| 4,285,073 | 8/1981 | Szycher | 3/13 |

FOREIGN PATENT DOCUMENTS

| | | |
|---|---|---|
| 976902 | 12/1964 | United Kingdom . |
| 980435 | 1/1965 | United Kingdom . |
| 1075467 | 7/1967 | United Kingdom . |
| 1240116 | 7/1971 | United Kingdom . |
| 1323766 | 7/1973 | United Kingdom . |
| 1351773 | 5/1974 | United Kingdom . |
| 1351774 | 5/1974 | United Kingdom . |
| 1401986 | 8/1975 | United Kingdom . |
| 1529319 | 10/1978 | United Kingdom . |

Primary Examiner—H. S. Cockeram
Attorney, Agent, or Firm—Kenway & Jenney

[57] ABSTRACT

A reaction product of 4,4' dicyclohexylmethane diisocyanate, polytetramethylene ether glycol and ethylene oxide-capped trimethylol propane. The resulting polyurethane is optically clear and suitable for use as an artificial cornea, or a permanently implantable lens.

2 Claims, 5 Drawing Figures

KERATOPROSTHETIC POLYURETHANE

This is a division of application Ser. No. 238,767, filed Feb. 27, 1981, which is a division of application Ser. No. 120,345, filed Feb. 11, 1980, now U.S. Pat. No. 4,285,073.

BACKGROUND OF THE INVENTION

This invention relates to correction of injured or defective eyes, and more particularly to a synthetic corneal implant in the nature of a biological window which can be permanently substituted for the damaged area in corneal tissue. By virtue of its clarity and biological compatibility, the material of this invention can also serve as a permanently implantable lens.

Occassionally the corneal tissue which overlies the fore part of the human eyeball becomes injured or a growth forms therein which will create opaque areas in the cornea. If such opaque or lumpy areas occur over the pupil, then the person thus afflicted will be blind or at least have his vision partially obscured.

Presently, when a cornea has become diseased to a point where replacement is warranted, the only truly effective method for such replacement is to perform a cornea transplant. Of course, the performance of a cornea transplant requires that a cornea be available and that the recipient be able to immunologically tolerate the transplant.

While the technique of making corneal transplants from eyes stored in so-called "eye banks" is highly developed, the percentage of successful operations is decidedly in the minority. Such operations are less than thirty (30) percent successful and the most reliable figures available indicate that in only sixteen (16) percent of the cases was there any improvement in visual acuity.

Present day practice in repairing damaged corneas involves replacing a carefully cut-out circular or square portion of the cornea with that of a donor which has been cut exactly to the same dimensions and configuration. The newly grafted cornea is then permitted to heal and form a transparent window through which the patient can see clearly. The operation is extremely critical and a high percentage of failures occurs because the corneal implant does not properly graft or will deteriorate, again becoming opaque. The major reasons for failure are clouding of the graft and ingrowth of blood vessels and these failures have suggested the desirability of an artificial graft into which the blood vessels could not grow, and around which granulation tissue would not cloud the normal field of vision. Such clouding conditions greatly decrease the number of cornea transplants that can be performed.

Various attempts have been made to provide such grafts in the form of synthetic windows. In these windows, various transparent materials have been used but even when these were sufficiently inert to be tolerated, the grafts, although sutured in place, soon extruded. It is, of course, highly desirable to have a synthetic material that can be used as an artificial cornea for a cornea transplant.

In order for a synthetic material to be successful for use in Keratoprosthesis, the material must meet a number of criteria. For example, the material must be compatible with the tissue in the human eye. The material must be optically clear. It must also be tough and easy to fabricate. Up to the present time, such a material which meets all of the foregoing criteria has not been found.

SUMMARY OF THE INVENTION

In accordance with the present invention, a polyurethane has been developed which is crystal clear and which can be used as an artificial cornea. The polyurethane is composed of the reaction product of:
1. 4,4' dicyclohexylmethane diisocyanate;
2. polytetramethylene ether glycol; and
3. ethylene oxide-capped trimethylol propane.

DESCRIPTION OF THE PREFERRED EMBODIMENT

At the outset, the invention is described in its broadest overall aspects with a more detailed description following. The polyurethane elastomer of the present invention is a rubbery reaction product of 4,4' dicyclohexylmethane diisocyanate, polytetramethylene ether glycol, and ethylene oxide-capped trimethylol propane.

In general, polyurethane polymers are the condensation products of reactions between diisocyanates and compounds containing active hydrogen sites such as hydroxyl groups. A diisocyanate is an isocyanate compound having a functionality of 2. The polymerization takes place in the presence of a difunctional hydroxyl compound (this can be either a simple glycol or a macromolecular glycol).

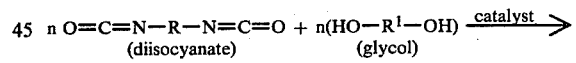

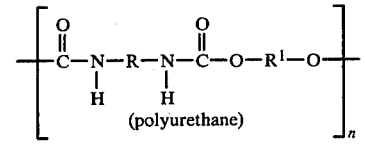

In the present invention, the diisocyanate is 4,4' dicyclohexylmethane diisocyanate which has the following structural formula:

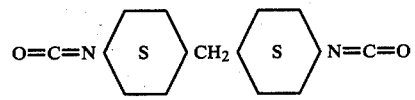

The difunctional hydroxyl compound is polytetramethylene ether glycol (PTMEG) H—(O—CH$_2$—CH$_2$—CH$_2$—CH$_2$)n—OH. In general to be useful in the present invention, this glycol should have an average molecular weight between about 500-5000, preferably between 1000–3000. In the preferred embodiment of the invention, the PTMEG has a molecular weight of 2000.

The polyurethane of the present invention also includes a chain extender (low molecular weight glycol). In accordance with the present invention, the chain extender is ethylene oxide-capped trimethylol propane which has the following structural formula:

$$\underset{\underset{HO-CH_2CH_2-O-CH_2}{|}}{\overset{\overset{CH_2-O-CH_2CH_2-OH}{|}}{CH_3-CH_2-C-CH_2-O-CH_2CH_2-OH}}$$

In preparing clear elastomeric polymers in accordance with the present invention, 2.2 equivalent weights of the 4,4′ dicyclohexylmethane diisocyanate is reacted with 1.0 equivalent weights of polytetramethylene ether glycol and 1.0 equivalent weights of ethylene oxide-capped trimethylol propane. The result of the reaction is a polyurethane elastomer having the following structural formula:

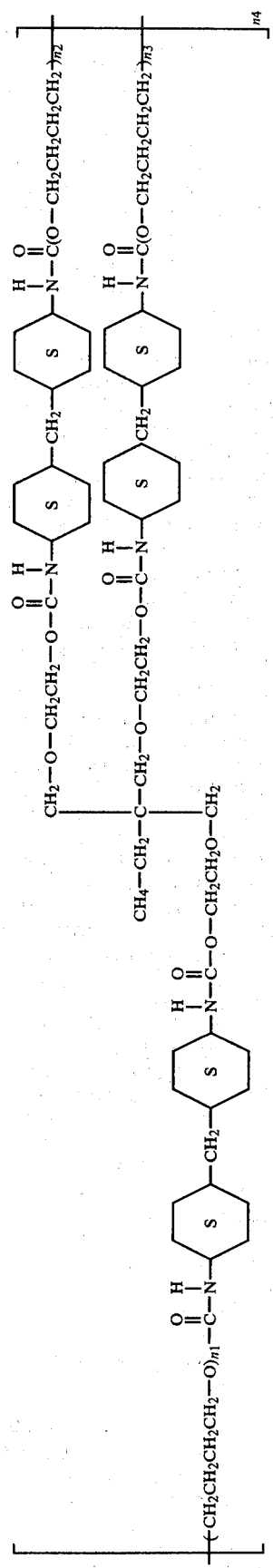

where $n_1$, $n_2$, and $n_3$ are positive integers between the range of 25-30 and $n_4$ is a positive integer between the range of 100-300.

To obtain fully cured polyurethane castings in a reasonably short period of time, it is customary to incorporate into the reaction mixture, a suitable catalyst to promote the polymerization reaction. Suitable catalysts include N-methylmorpholine, trimethyl amine, triethyl amine, zinc octoate and dibutyl tin dilaurate. Dibutyl tin dilaurate is the preferred catalyst.

Figure 2:
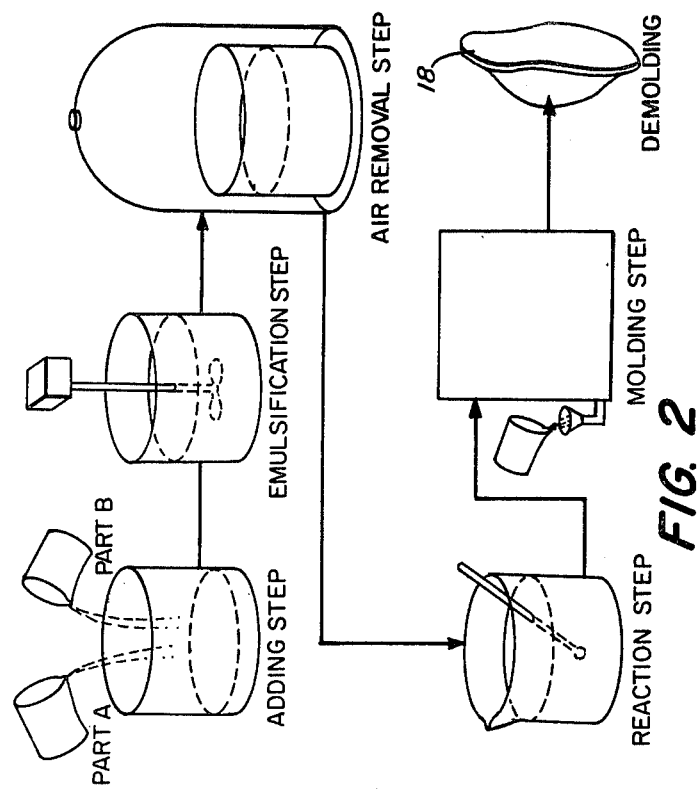
FIG. 2 is a diagram illustrating the process in accordance with the present invention for molding corneas from the elastomer of the present invention.

The process for molding a cornea in accordance with the present invention is represented diagrammatically in FIG. 2. In practicing the invention, the polyurethane is prepared from two components which can be referred to as part A and part B. Part A is the aliphatic diisocyanate, that is 4,4' dicyclohexylmethane diisocyanate. Part B is comprised of the remaining constituents, that is the polytetramethylene ether glycol, the ethylene oxide-capped trimethylol propane and the catalyst. To form a polyurethane molded element, such as a cornea or a lens, the proper stoichiometric proportions of part A and part B are emulsified in a mixture at room temperature to form a moderately reactive thixotropic mixture having a viscosity below about 2500 cps.

Since the emulsification introduces air into the reactive mixture, the air must be removed. The air bubbles are removed by placing a vessel containing the emulsion under a bell jar and evacuating the air from the bell jar with a suction device. The bell jar is evacuated to a pressure of about 0.3 microns and the mixture is kept under the bell jar about 8 minutes causing the mixture to appear to boil. After the emulsion is taken from the bell jar, it is allowed to stand until the exothermic reaction that is taking place brings it to a temperature of about 40° C. At that point, the emulsion is forced into a mold.

It is preferred to force the emulsion from the bottom to the top of the mold by the use of a pressurizing gas such as dry nitrogen. After the mold is filled, it is placed in an oven and heated to a temperature of at least 110° C. for four hours or more until the elastomer is cured. The mold is then removed from the oven, allowed to reach room temperature and the cornea or lens is demolded. It is anticipated that a single mold will actually be used to form several corneas or lenses which are connected together. After being removed from the mold, the corneas or lenses are trimmed. The cornea molds are designed such that a thickness of 250 micrometers or less can be achieved for a given cornea.

The invention is further illustrated by the following nonlimiting examples.

EXAMPLE 1

One Shot Technique

A blend of polytetramethylene ether glycol, molecular weight 2000, and ethylene-oxide capped trimethylol propane is heated to 35° and degassed for several minutes. Mixing ratio by weight is 227.2 grams of polyether to 24.9 grams of triol. To insure proper cure, 0.015 grams of dibutyl tin dilaurate are added to the above mixture. To this blend is charged 67.9 grams of 4,4' dicyclohexylmethane diisocyanate and both materials are intimately emulsified by mixing for three minutes. This is followed by a second degassing step to remove any entrapped air in the blend.

The batch is forced into a suitable mold by means of nitrogen pressure and cured at 110° C. for 3 hours. This results in optically clear, elastic polymer with the following physical properties: 320 psi ultimate tensile strength; 600% elongation; and a Shore A hardness of 65.

Figure 4:
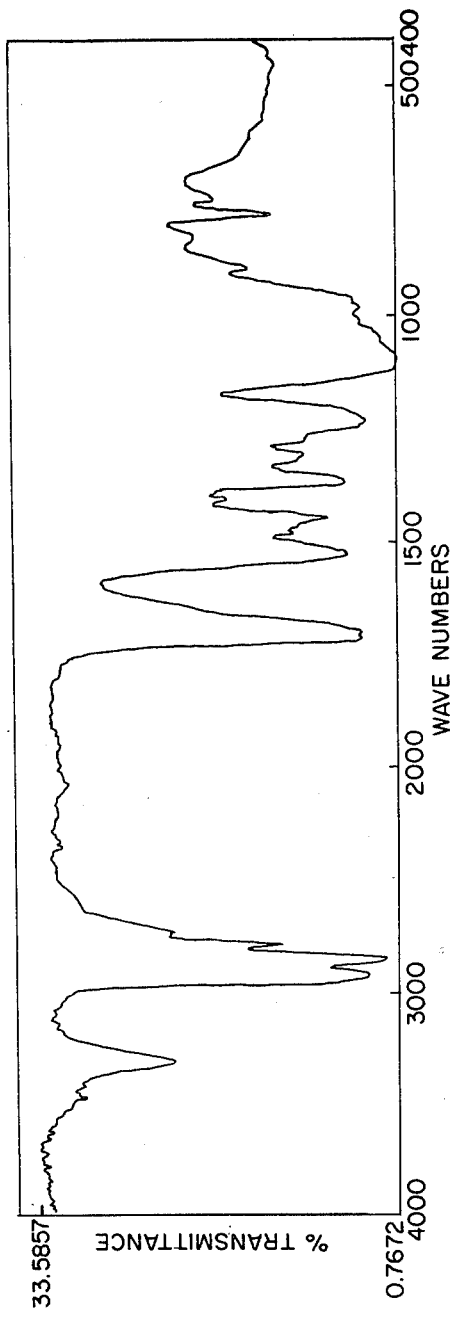
FIGS. 4 and 5 are infra-red spectra of the polymer of the present invention.
Figure 5:
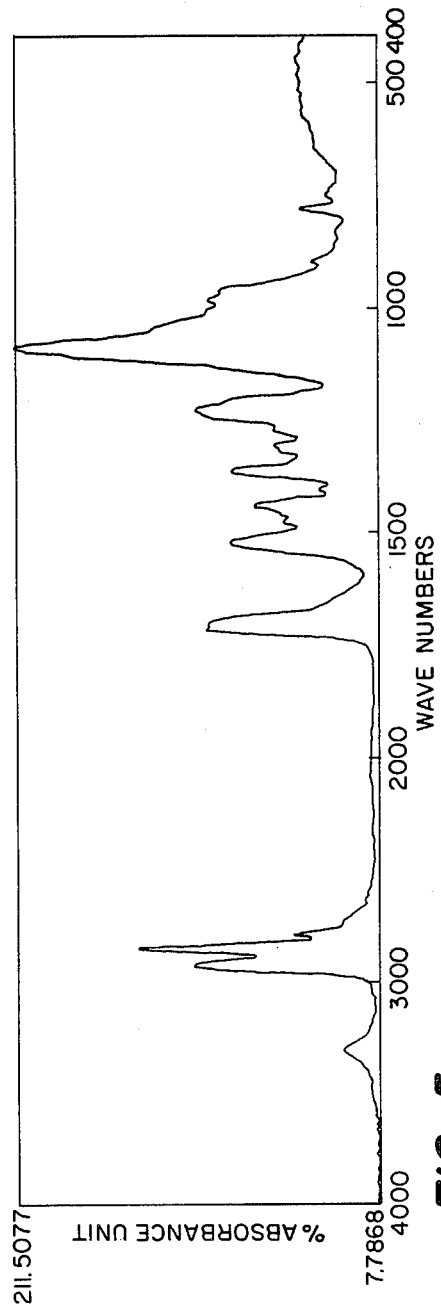

An infrared spectrum of a polymer in accordance with the present invention is shown in FIGS. 4 and 5. FIG. 4 is the transmittance infrared spectrum and FIG. 5 is the absorbance spectrum.

Material prepared by the procedures set forth in Example 1 has been inserted beneath the cornea of one eye of a rabbit. This was done by making a surgical incision in the cornea of the rabbit and slipping a piece of the material underneath the existing cornea. This test demonstrated that the rabbit was able to see out of the eye containing the material of the present invention, which remained clear and free of opacifying blood vessels for the entire implantation test period of 30 days.

Figure 3:
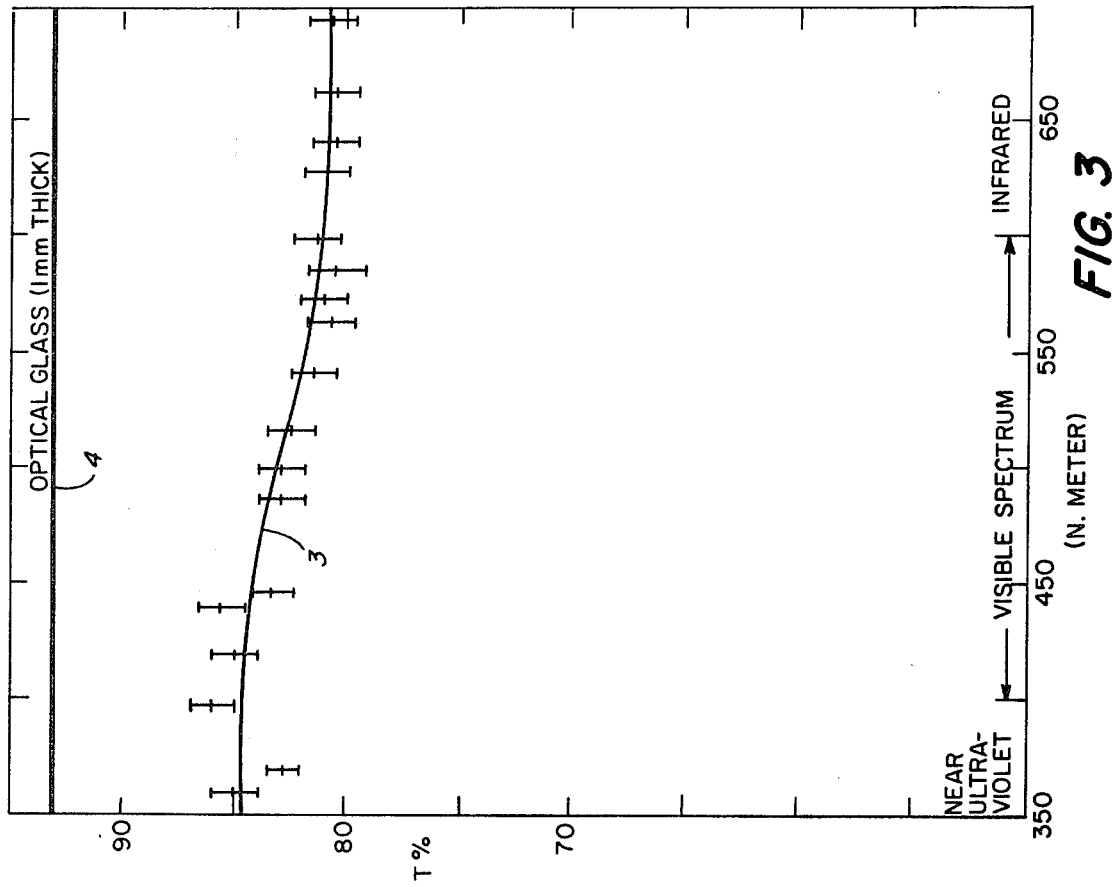
FIG. 3 is a graph of light transmissive characteristics of the polymer of the present invention.

FIG. 3 illustrates the clarity of the polymer of the present invention by comparing its light transmissivity with that of a high quality optical glass. Curve 3 represents the polymer of the present invention; and, curve 4 represents a high quality optical glass.

Figure 1:
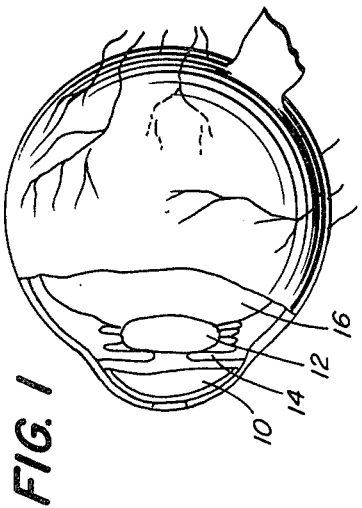
FIG. 1 is a schematic view of an eye showing a cornea formed of material in accordance with the present invention.

In order that the keratoprosthetic procedure in accordance with the invention may be readily understood, reference is made to the fact that a cornea 10 protrudes somewhat from the regular contour of the remainder of the eyeball. (See FIG. 1.) Other parts of the eyeball that are shown in FIG. 1 are the lens 12, the iris 14, and the vitreous body 16. As is stated above, lens 12 can be formed of a polymer in accordance with the present invention and can be implanted in an eyeball.

Before detailing the implant 18 of FIG. 2, it is to be noted that it is relatively thin and of concavo-convex form to approximate the contour of the affected cornea 10. To accommodate an implant in accordance with the invention, the cornea 10 is divided by an incision, separating the cornea into anterior and posterior layers with the layers remaining interconnected in the zone of the limbus, the zone usually being diametrically opposite to the area in which the incision was started.

After the completion of the incision, the anterior layer is laid back and the implant is then positioned on the posterior corneal layer. The layer is drawn over the thus located implant and sutured so that the implant is held in place between the corneal layers.

As has been stated above, the material of the present invention is suitable for forming an artificial lens which can be surgically implanted into an eyeball. Often a lens becomes clouded resulting in vision impairment. When such a condition occurs, a lens formed of the polymer in accordance with the invention can be used as a replacement for the patient's normal lens. In performing such a procedure, the existing lens 12 will be removed by known techniques. One such technique is to break up the lens into small pieces and remove the small pieces from the eyeball by a suction device. With the normal lens removed, a lens formed of the polymer in accordance with the present invention having about the same physical shape can be inserted into the eyeball and secured in place in a manner similar to that described above with regard to the placement of the artificial cornea.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A polyurethane elastomer, said polyurethane elastomer being the reaction product of, 2.2 equivalent weights of 4,4' dicyclohexylmethane diisocyanate, 1.0 equivalent weights of polytetramethylene ether glycol wherein the molecular weight of said polytetramethylene ether glycol is between the range of 1000–3000, and 1.0 equivalent weights of ethylene oxide-capped trimethylol propane.

2. A polyurethane elastomer having the following formula:

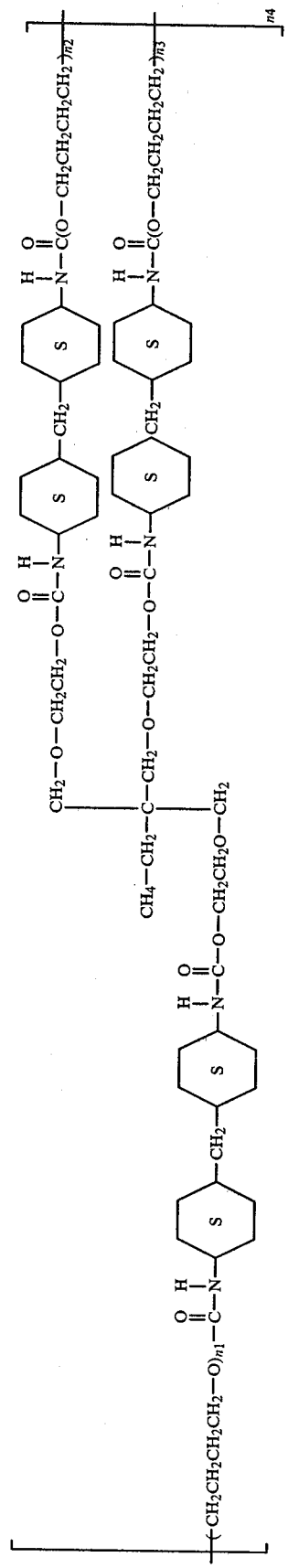

where $n_1$, $n_2$ and $n_3$ are positive integers between the range of 25-30 and $n_4$ is a positive integer between the range of 100-300.

* * * * *